(12) United States Patent
Schulte

(10) Patent No.: US 7,331,613 B2
(45) Date of Patent: Feb. 19, 2008

(54) MEDICAL TUBING CONNECTOR ASSEMBLY INCORPORATING STRAIN RELIEF SLEEVE

(75) Inventor: Gregory T. Schulte, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 204 days.

(21) Appl. No.: 10/844,962

(22) Filed: May 13, 2004

(65) Prior Publication Data

US 2005/0253389 A1    Nov. 17, 2005

(51) Int. Cl.
*F16L 47/00* (2006.01)

(52) U.S. Cl. ............ 285/239; 285/256; 285/382; 285/397; 285/417

(58) Field of Classification Search ........... 285/239, 285/256, 382, 382.1, 382.2, 382.4, 382.5, 285/398, 417, 258, 370–371, 397, 131.1; 604/241, 533
See application file for complete search history.

(56) References Cited

U.S. PATENT DOCUMENTS

| | | | |
|---|---|---|---|
| 2,815,227 A | 12/1957 | Cullen et al. ............. 285/23 |
| 3,447,819 A | 6/1969 | Borsum et al. ........... 285/111 |
| 3,731,955 A | 5/1973 | Borsum et al. ........... 285/111 |
| 4,013,310 A | 3/1977 | Dye ....................... 285/110 |
| 4,193,616 A | 3/1980 | Sarson et al. ............. 285/39 |
| 4,310,001 A | 1/1982 | Comben .................. 607/37 |
| 4,323,065 A | 4/1982 | Kling ..................... 604/533 |
| 4,334,551 A | 6/1982 | Pfister ................. 137/614.03 |
| 4,405,163 A | 9/1983 | Voges et al. ............. 285/305 |
| 4,526,572 A | 7/1985 | Donnan et al. ............ 604/29 |
| 4,581,012 A | 4/1986 | Brown et al. ............. 604/43 |
| 4,592,749 A | 6/1986 | Ebling et al. ............ 604/533 |
| 4,610,468 A | 9/1986 | Wood ..................... 285/81 |
| 4,632,435 A | 12/1986 | Polyak .................. 285/243 |
| 4,635,972 A * | 1/1987 | Lyall ..................... 285/242 |
| 4,636,204 A | 1/1987 | Christopherson et al. ... 604/535 |
| 4,650,473 A | 3/1987 | Bartholomew et al. ..... 604/174 |
| 4,673,394 A | 6/1987 | Fenton, Jr. et al. ........ 604/175 |
| 4,675,007 A | 6/1987 | Terry ..................... 604/533 |
| 4,691,943 A | 9/1987 | DeLand et al. ........... 285/315 |
| 4,701,159 A | 10/1987 | Brown et al. .............. 604/43 |
| 4,704,103 A | 11/1987 | Stöber et al. ............ 604/175 |
| 4,723,948 A | 2/1988 | Clark et al. ............. 604/533 |

(Continued)

FOREIGN PATENT DOCUMENTS

AU    A-21021/83    5/1985

(Continued)

OTHER PUBLICATIONS

U.S. Appl. No. 11/057,666, filed Feb. 14, 2005, Cross.
U.S. Appl. No. 11/087,927, filed Mar. 23, 2005, Hegland et al.

*Primary Examiner*—Aaron Dunwoody
*Assistant Examiner*—Fannie C. Kee
(74) *Attorney, Agent, or Firm*—Mueting, Raasch & Gebhardt, P.A.

(57) ABSTRACT

A connector assembly for interconnecting separate sections of tubing, e.g., medical tubing. Connector assemblies are a two-piece construction having a connector pin and a connector sleeve. The connector sleeve includes a first end, a second end, and a passageway extending between the first and second ends. The passageway is stepped, e.g., defined by both a bore of a first diameter and a bore of a second diameter.

17 Claims, 4 Drawing Sheets

U.S. PATENT DOCUMENTS

| | | | |
|---|---|---|---|
| 4,772,276 A | 9/1988 | Wiita et al. | 604/533 |
| 4,781,185 A | 11/1988 | Kauphusman et al. | 606/2 |
| 4,786,089 A | 11/1988 | McConnell | 285/281 |
| 4,823,805 A | 4/1989 | Wojcik | 600/549 |
| 4,834,719 A | 5/1989 | Arenas | 604/243 |
| 4,850,984 A | 7/1989 | Harris | 604/326 |
| 4,880,414 A | 11/1989 | Whipple | 604/533 |
| 4,890,866 A | 1/1990 | Arp | 285/243 |
| 4,895,570 A | 1/1990 | Larkin | 604/411 |
| 4,929,236 A | 5/1990 | Sampson | 604/175 |
| 4,929,243 A | 5/1990 | Koch et al. | 604/533 |
| 4,963,133 A | 10/1990 | Whipple | 604/533 |
| 4,983,161 A | 1/1991 | Dadson et al. | 604/28 |
| 4,994,048 A | 2/1991 | Metzger | 604/533 |
| 5,000,614 A | 3/1991 | Walker et al. | |
| 5,040,831 A | 8/1991 | Lewis | |
| 5,053,015 A | 10/1991 | Gross | 604/167.02 |
| 5,129,891 A | 7/1992 | Young | 604/533 |
| 5,167,647 A | 12/1992 | Wijkamp et al. | 604/532 |
| 5,178,612 A | 1/1993 | Fenton, Jr. | 604/533 |
| 5,209,740 A | 5/1993 | Bryant et al. | 604/243 |
| 5,226,898 A | 7/1993 | Gross | 604/243 |
| 5,257,622 A | 11/1993 | Hooper et al. | 607/37 |
| 5,279,597 A | 1/1994 | Dassa et al. | 604/535 |
| 5,312,337 A | 5/1994 | Flaherty et al. | 285/278 |
| 5,330,449 A | 7/1994 | Prichard et al. | 604/533 |
| 5,354,282 A | 10/1994 | Bierman | 604/180 |
| 5,360,418 A | 11/1994 | Weilbacher et al. | 604/534 |
| 5,380,301 A | 1/1995 | Prichard et al. | 604/533 |
| 5,387,192 A | 2/1995 | Glantz et al. | 604/288.02 |
| 5,399,168 A | 3/1995 | Wadsworth, Jr. et al. | 604/175 |
| 5,405,339 A | 4/1995 | Kohnen et al. | 604/535 |
| 5,417,672 A | 5/1995 | Nita et al. | 604/533 |
| 5,423,775 A | 6/1995 | Cannon | |
| 5,456,671 A | 10/1995 | Bierman | 604/180 |
| 5,466,230 A | 11/1995 | Davila | 604/256 |
| 5,551,849 A | 9/1996 | Christiansen | 417/472 |
| 5,562,618 A | 10/1996 | Cai et al. | 604/288.02 |
| 5,578,013 A | 11/1996 | Bierman | 604/180 |
| 5,613,945 A | 3/1997 | Cai et al. | 604/288.02 |
| 5,632,729 A | 5/1997 | Cai et al. | 604/288.01 |
| 5,637,102 A | 6/1997 | Tolkoff et al. | 604/536 |
| 5,702,371 A | 12/1997 | Bierman | 604/180 |
| 5,743,873 A | 4/1998 | Cai et al. | 604/288.02 |
| 5,827,230 A | 10/1998 | Bierman | 604/174 |
| 5,830,401 A | 11/1998 | Prichard et al. | 264/262 |
| 5,833,275 A | 11/1998 | Anderson | 285/305 |
| 5,913,852 A | 6/1999 | Magram | 604/540 |
| 5,947,931 A | 9/1999 | Bierman | 604/180 |
| 5,957,968 A | 9/1999 | Belden et al. | 607/126 |
| 5,971,958 A | 10/1999 | Zhang | 604/165.02 |
| 5,993,437 A | 11/1999 | Raoz | 604/536 |
| 6,068,622 A | 5/2000 | Sater et al. | 604/524 |
| 6,074,379 A | 6/2000 | Prichard | 604/524 |
| 6,113,572 A | 9/2000 | Gailey et al. | 604/93.01 |
| 6,231,548 B1 | 5/2001 | Bassett | 604/174 |
| 6,234,973 B1 | 5/2001 | Meador et al. | 600/486 |
| 6,238,374 B1 | 5/2001 | Winkler | 604/256 |
| 6,254,589 B1 | 7/2001 | Raoz | 604/536 |
| 6,273,404 B1 | 8/2001 | Holman et al. | 264/276 |
| 6,290,676 B1 | 9/2001 | Bierman | 604/180 |
| 6,332,874 B1 | 12/2001 | Eliasen et al. | 604/174 |
| 6,350,260 B1 | 2/2002 | Goebel et al. | 604/533 |
| 6,423,053 B1 | 7/2002 | Lee | 604/533 |
| 6,428,515 B1 | 8/2002 | Bierman et al. | 604/174 |
| 6,447,020 B1 * | 9/2002 | Kacines et al. | 285/256 |
| 6,453,185 B1 | 9/2002 | O'Keefe | 600/378 |
| 6,517,115 B1 | 2/2003 | Blivet | 285/23 |
| 6,517,520 B2 | 2/2003 | Chang et al. | 604/164.11 |
| 6,554,802 B1 | 4/2003 | Pearson et al. | 604/177 |
| 6,562,023 B1 | 5/2003 | Marrs et al. | 604/533 |
| 6,607,504 B2 | 8/2003 | Haarala et al. | 604/93.01 |
| 6,612,624 B1 | 9/2003 | Segal et al. | 285/330 |
| 6,641,177 B1 | 11/2003 | Pinciaro | 285/242 |
| 6,652,489 B2 | 11/2003 | Trocki et al. | |
| 6,673,046 B2 | 1/2004 | Bierman et al. | 604/174 |
| 6,676,652 B2 | 1/2004 | Mogg | 604/535 |
| 6,679,528 B1 | 1/2004 | Poder | 285/305 |
| 6,740,101 B2 | 5/2004 | Houser et al. | 606/153 |
| 6,749,231 B2 | 6/2004 | LeMay et al. | 285/93 |
| 6,749,574 B2 | 6/2004 | O'Keefe | 600/561 |
| 6,796,586 B2 | 9/2004 | Werth | 285/243 |
| 6,799,991 B2 | 10/2004 | Williams et al. | 439/482 |
| 6,802,490 B2 | 10/2004 | Leinsing et al. | 251/149.6 |
| 6,802,836 B2 | 10/2004 | Bouphavichith et al. | 604/534 |
| 6,817,995 B1 | 11/2004 | Halpern | 604/524 |
| 6,893,424 B2 | 5/2005 | Shchervinsky | 604/264 |
| 2001/0049519 A1 | 12/2001 | Holman et al. | 604/534 |
| 2002/0079696 A1 | 6/2002 | Szabo | |
| 2002/0082559 A1 | 6/2002 | Chang et al. | 604/164.09 |
| 2003/0004520 A1 | 1/2003 | Haarala et al. | 606/108 |
| 2003/0045912 A1 | 3/2003 | Williams et al. | 607/37 |
| 2003/0077935 A1 | 4/2003 | Stein et al. | 439/482 |
| 2003/0158539 A1 | 8/2003 | Bouphavichith et al. | 604/533 |
| 2003/0199853 A1 | 10/2003 | Olsen et al. | 604/535 |
| 2004/0039373 A1 | 2/2004 | Harding et al. | 604/533 |
| 2004/0102736 A1 | 5/2004 | Bierman | 604/180 |
| 2004/0111056 A1 | 6/2004 | Weststrate et al. | 604/104 |
| 2004/0127854 A1 | 7/2004 | Leinsing et al. | 604/167.03 |
| 2004/0204690 A1 | 10/2004 | Yashiro et al. | 604/257 |
| 2005/0033371 A1 | 2/2005 | Sommer et al. | 607/37 |
| 2005/0143714 A1 | 6/2005 | Hegland et al. | 604/533 |

FOREIGN PATENT DOCUMENTS

| | | |
|---|---|---|
| DE | 24 56 166 | 8/1976 |
| DE | 90 13 145 U1 | 1/1991 |
| EP | 0 474 266 A2 | 3/1992 |
| EP | 0 474 266 A3 | 3/1992 |
| EP | 0 332 943 B1 | 9/1992 |
| EP | 0 505 930 A2 | 9/1992 |
| EP | 0 505 930 A3 | 1/1993 |
| EP | 0 343 910 B1 | 6/1993 |
| EP | 0 360 471 B1 | 4/1994 |
| EP | 0 415 665 B1 | 1/1995 |
| EP | 0 505 930 B1 | 6/1996 |
| EP | 0 229 729 B1 | 8/1996 |
| EP | 0 552 180 B1 | 12/1996 |
| EP | 0 678 302 B1 | 2/1999 |
| EP | 0 930 083 A2 | 7/1999 |
| EP | 0 930 083 A3 | 7/1999 |
| EP | 1 138 343 A1 | 10/2001 |
| EP | 1 181 946 A1 | 2/2002 |
| EP | 1 186 316 A2 | 3/2002 |
| EP | 1 186 316 A3 | 3/2002 |
| EP | 0 691 868 B1 | 6/2002 |
| EP | 1 033 146 B1 | 7/2002 |
| EP | 1 219 319 A1 | 7/2002 |
| EP | 1 466 645 A2 | 10/2004 |
| FR | 2 586 569 | 3/1987 |
| FR | 2 612 784 | 9/1988 |
| FR | 2 750 055 | 7/1998 |
| GB | 2 343 723 A | 5/2000 |
| WO | WO 93/05844 A1 | 4/1993 |
| WO | WO 94/21319 A1 | 9/1994 |
| WO | WO 94/23775 A1 | 10/1994 |
| WO | WO 95/19801 A1 | 7/1995 |
| WO | WO 95/19802 A1 | 7/1995 |
| WO | WO 97/25562 | 7/1997 |
| WO | WO 99/53981 A1 | 10/1999 |
| WO | WO 00/13743 A1 | 3/2000 |
| WO | WO 00/24462 A1 | 5/2000 |
| WO | WO 01/91825 A2 | 12/2001 |
| WO | WO 01/91825 A3 | 12/2001 |

| | | |
|---|---|---|
| WO | WO 01/91847 A2 | 12/2001 |
| WO | WO 01/91847 A3 | 12/2001 |
| WO | WO 03/002171 A1 | 1/2003 |
| WO | WO 03/020368 A2 | 3/2003 |
| WO | WO 03/070151 A2 | 8/2003 |
| WO | WO 03/090840 A1 | 11/2003 |
| WO | WO 2004/016309 A2 | 2/2004 |
| WO | WO 2004/016309 A3 | 2/2004 |
| WO | WO 2004/018015 A2 | 3/2004 |
| WO | WO 2004/018015 A3 | 3/2004 |
| WO | WO 2004/052272 A2 | 6/2004 |
| WO | WO 2004/052272 A3 | 6/2004 |
| WO | WO 2004/060466 A1 | 7/2004 |
| WO | WO 2005/030316 A1 | 4/2005 |

* cited by examiner

MEDICAL TUBING CONNECTOR ASSEMBLY INCORPORATING STRAIN RELIEF SLEEVE

TECHNICAL FIELD

The present invention relates generally to medical devices and, more particularly, to connector assemblies for joining two pieces of medical tubing, e.g., catheters, wherein the connector assemblies are operable to provide strain relief to the catheter connection.

BACKGROUND

In many medical applications, it is necessary to connect one section of medical tubing, e.g., a catheter, with another. Generally speaking, it is important that these connections be relatively secure and stable so that the tubing does not separate or develop leaks at the connection point. Security and leak-resistance take on special importance in applications where the tubing sections are implanted in a human body.

One procedure that necessitates implantation of medical tubing into the body involves the use of an implantable drug infusion pump. Such pumps are often used to control pain and/or spasticity, as well as to provide one or more drugs or fluid medications to a particular location within the body. For instance, a typical implant procedure may involve implanting a drug infusion pump into a cavity or subcutaneous pocket in the body and delivering a drug, via a catheter(s), to an epidural space or intrathecal space of the spinal column or to a particular location within the brain. In this exemplary application, a catheter assembly having two or more catheter sections, e.g., a thin-walled distal section (near the implantation site) and a thicker-walled proximal section (connected directly to the infusion pump), may be used to deliver the drug to the desired site.

The distal catheter section may be positioned in the desired location in the body and then connected to the proximal catheter section by use of a medical tubing connector. The connection may be made by inserting one end or prong of the connector into a lumen of one catheter section (e.g., the proximal section) and the other end of the connector into the lumen of the other catheter section (e.g., the distal section) and then sliding both catheter sections towards one another (toward the middle of the connector). The proximal section may then be connected to the drug infusion pump.

While adequate, difficulties have been encountered in the manufacture and use of such prior art medical connectors. For example, these connectors, which have been sized to fit within the lumens of the catheter tubing sections, are small and may be difficult to manipulate during implantation. Moreover, because some of these connectors fit entirely within the lumens of the respective catheter sections, it is often difficult for the implanting physician to be sure that the interface between catheter sections is positioned at, or even near, the center of the connector, i.e., it may be difficult to center the catheter sections on the connector. Misalignment of the connector can result in a weakened connection that is more likely to separate and/or develop leaks. Other potential problems include: lack of ability to adequately secure the catheters relative to one another; and inability to provide sufficient strain relief to the connection.

SUMMARY OF THE INVENTION

Embodiments of the present invention provide connector assemblies and methods for connecting sections of medical tubing that may overcome some or all of the problems identified above. For example, in one embodiment, a connector assembly is provided having a connector pin. The connector pin includes: a first end portion, a second end portion, and a lumen extending between the first end portion and the second end portion; and a central portion located between the first end portion and the second end portion, wherein the central portion has an outer dimension that is larger than an outer dimension of both the first and second end portions. The assembly also includes a tubular connector sleeve comprising a first end, a second end, and a passageway extending between the first end and the second end. The passageway is stepped such that it has: a first diameter between the first end of the sleeve and a stop surface located in the passageway; and a second diameter between the stop surface and the second end of the sleeve, wherein the first diameter is greater than the second diameter.

In another embodiment, a method of interconnecting sections of medical tubing is provided, wherein the method includes inserting a first end portion of a connector pin into a first medical tube. The connector pin includes: a second end portion, wherein a lumen extends between the first end portion and the second end portion; and a central portion located between the first and second end portions, wherein the central portion includes an outer dimension that is greater than an outer dimension of either of the first and second end portions. The method also includes: inserting the second end portion into a second medical tube; sliding a tubular sleeve over the first and second medical tubes and the connector pin; and engaging a first lock portion located within a passageway of the sleeve with a second lock portion of the connector pin.

The above summary is not intended to describe each embodiment or every implementation of the present invention. Rather, a more complete understanding of the invention will become apparent and appreciated by reference to the following Detailed Description of Exemplary Embodiments and claims in view of the accompanying figures of the drawing.

BRIEF DESCRIPTION OF THE VIEWS OF THE DRAWING

The present invention will be further described with reference to the figures of the drawing, wherein:

FIGS. 6-7 illustrate an exemplary method for assembling the connector assembly of FIGS. 1 and 2; wherein FIG. 6 illustrates the connector pin during insertion into the tubular connector sleeve; and FIG. 7 illustrates the connector pin after complete insertion into the sleeve.

DETAILED DESCRIPTION OF EXEMPLARY EMBODIMENTS

Figure 1:
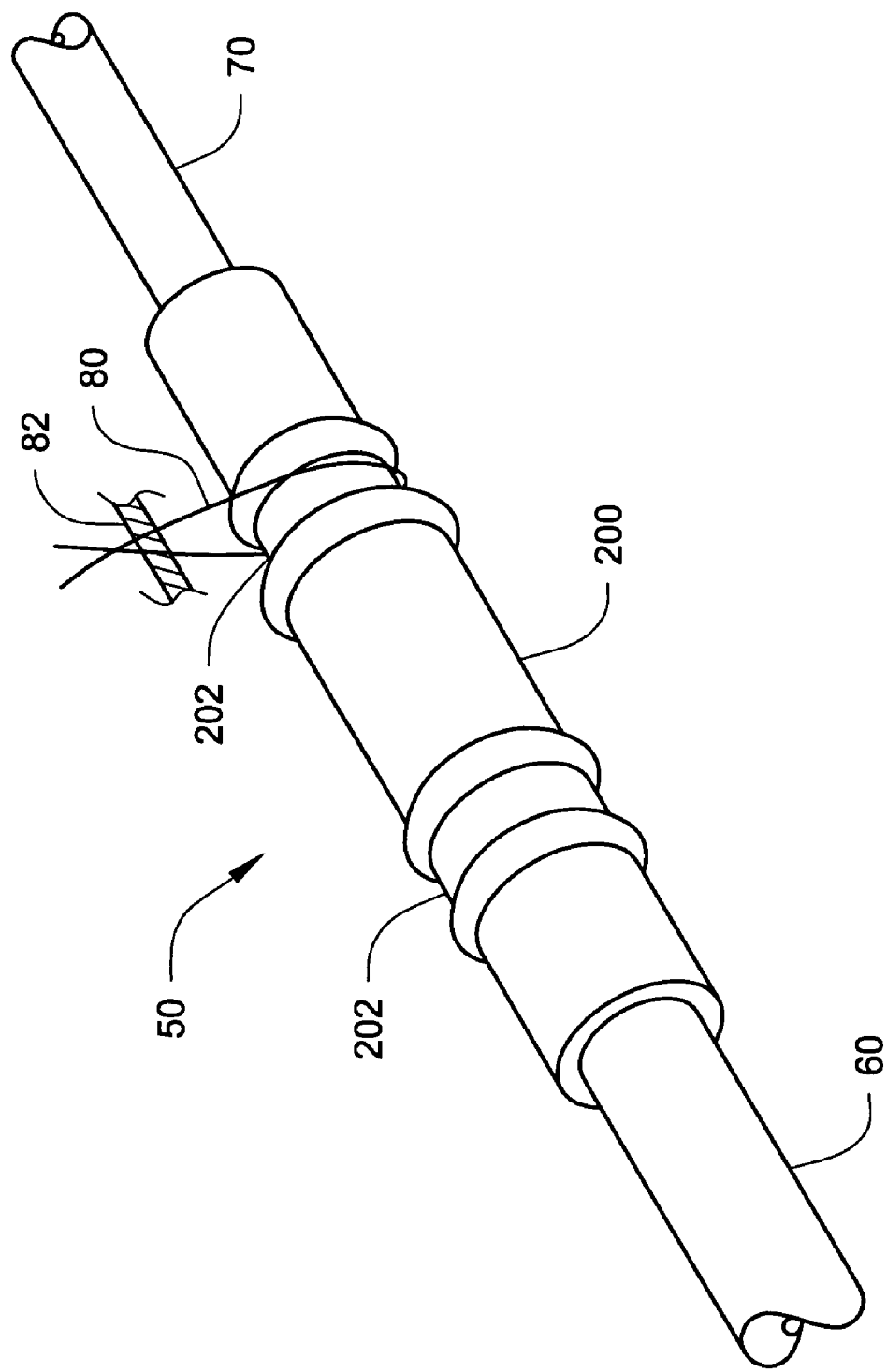
FIG. 1 is a perspective view of a connector assembly in accordance with one exemplary embodiment of the invention, the connector assembly for use with coupling separate sections of medical tubing, e.g., catheters.

In the following detailed description of illustrative embodiments of the invention, reference is made to the accompanying figures of the drawing which form a part hereof, and in which are shown, by way of illustration, specific embodiments in which the invention may be practiced. It is to be understood that other embodiments may be utilized and structural changes may be made without departing from the scope of the present invention. Unless stated otherwise herein, the figures of the drawing are rendered primarily for clarity and thus may not be drawn to scale.

Generally speaking, the invention is directed to apparatus and methods for securely coupling two pieces of tubing to one another. While the invention may find application to most any type of tubing, it is especially well-suited to the joining of separate sections of medical tubing, e.g., catheters. For instance, connector assemblies in accordance with embodiments of the present invention may be used to couple a drug infusion catheter (extending from a drug infusion pump) to a brain infusion catheter located at a predetermined location within a human brain. Accordingly, while the following exemplary embodiments are described with reference to such infusion catheter couplings and methods, those of skill in the art will realize that the invention may find use with most any type of tubing application.

Figure 2:
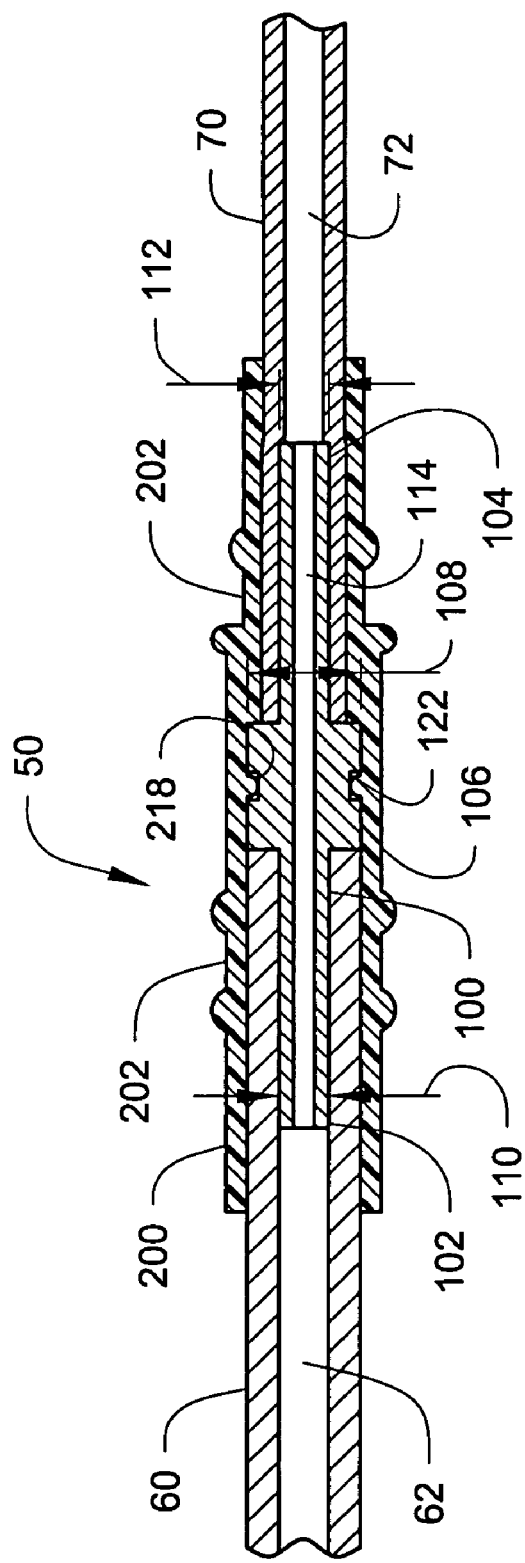
FIG. 2 is a cross-sectional view of the connector assembly of FIG. 1.

FIGS. 1 and 2 illustrate a medical tubing connector assembly 50 in accordance with one embodiment of the invention. The assembly 50 may include a medical connector, e.g., connector pin 100 (see FIG. 2), and a strain relieving, tubular connector sleeve 200. A first medical tubing section, e.g., first catheter 60, and a second tubing section, e.g., second catheter 70, may couple to the connector pin 100 as further described below. Once so coupled, the tubular sleeve 200 may slide over the connector pin 100 and the catheters 60 and 70 as shown, resulting in a secure and substantially leak-free coupling of the independent catheters.

Moreover, as further explained below, the connector assembly 50 may provide strain relief for the catheters 60 and 70. That is, the tubular connector sleeve 200 may provide resistance to tearing of the catheters 60 and 70 by the ends of connector pin 100 and further resist forces that would tend to separate, or allow relative movement of, the connector pin 100 relative to the catheters 60 and 70. The connector assembly 50 may also include securing features, e.g., suture grooves 202 on an exterior surface of the sleeve 200, to permit securing the sleeve 200 over the connector pin 100 and for fixing of the assembly relative to local tissue 82, e.g., with a suture 80.

FIG. 2 illustrates a cross section of the connector assembly 50. In this view, the connector pin 100 is illustrated as a generally longitudinal member having a first end portion 102 (also shown in FIG. 3) operable to fit within a lumen 62 of the first catheter 60 with a small clearance fit or, alternatively, an interference fit, and a second end portion 104 operable to fit within a lumen 72 of the second catheter 70 with small clearance, or interference, fit. The fits between the connector pin 100 and the catheters 60 and 70 may be sufficient to hold the catheters in place, relative to the connector pin, under normal operating circumstances.

The connector pin 100 may also include a central portion 106 positioned between the first end portion 102 and the second end portion 104. The central portion 106 has an outer or external dimension, e.g., a diameter 108, that is preferably larger than at least one of: an outer or external dimension (e.g., a first diameter 110) of the first end portion 102; and an outer or external dimension (e.g., a second diameter 112) of the second end portion 104. The connector pin 100 may also include a lumen 114 extending through the pin from the first end portion 102 to the second end portion 104. The lumen 114, in the illustrated embodiment, may pass completely through the connector pin 100 so as to permit fluid communication between the first catheter 60 and the second catheter 70.

Figure 3:
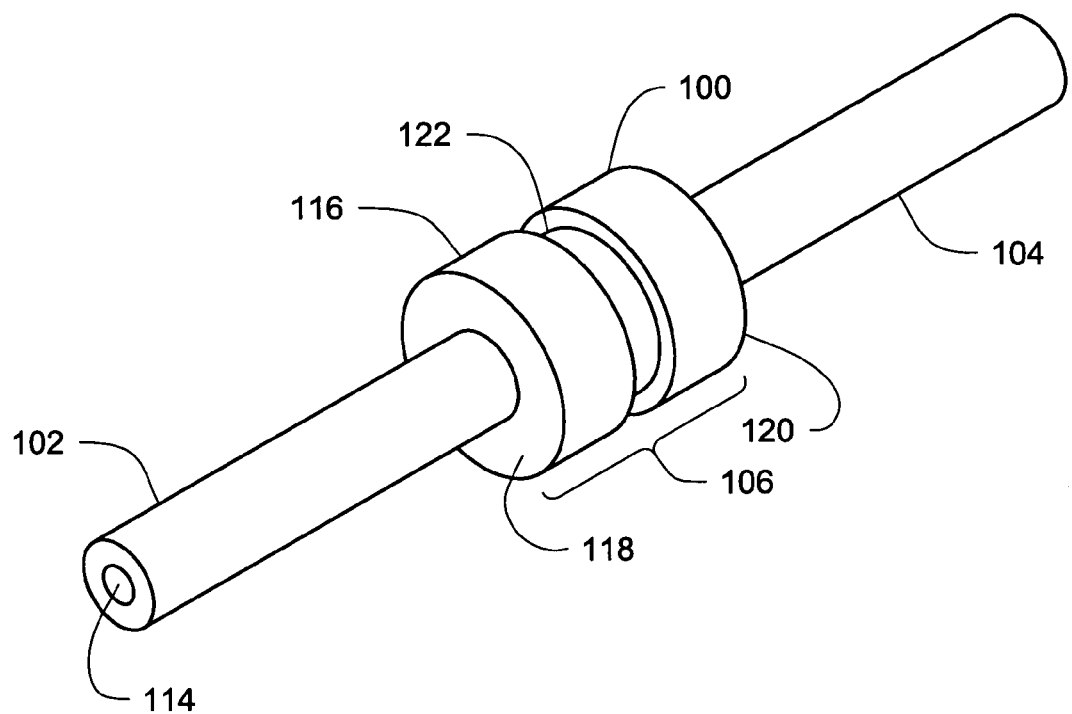
FIG. 3 is a perspective view of a connector pin in accordance with one embodiment of the present invention.

FIG. 3 is an enlarged perspective view of the exemplary connector pin 100 of FIG. 2. The connector pin 100 may be made of most any biocompatible material including various metals and plastics, e.g., noble metals such as titanium. Moreover, the connector pin 100 may be an integral component or, alternatively, the enlarged central portion 106 may be made of a secondary material which may, for example, be molded to a shaft formed by the first and second end portions. In the illustrated embodiments, the lumen 114 may be generally concentric to the longitudinal axis of the connector pin 100.

The end portions 102 and 104 may extend a sufficient distance from the central portion 106 to ensure adequate engagement with the catheters 60 and 70. Moreover, while the end portions 102 and 104 may be most any shape, they are preferably cylindrical to correspond with the shape of the catheter lumens into which they are inserted. The enlarged central portion 106 may also be of most any shape but is also preferably cylindrical to correspond to the shape of the tubular connector sleeve 200 as further described below.

In the embodiment illustrated in FIG. 3, enlarged central portion 106 may include an outer surface 116 bounded by stop surfaces 118 and 120, which are generally perpendicular to a longitudinal axis of the connector pin 100. The stop surfaces 118 and 120 may provide a positive stop against which the ends of the catheters 60 and 70, respectively, abut when the connector pin 100 is inserted therein. By providing the stop surfaces 118 and 120, the physician may ensure that each catheter is properly engaged with the connector pin 100. The stop surface 120 may also assist the physician in locating the tubular connector sleeve 200 relative to the connector pin 100 as further described below.

The central portion 106 may further include a lock portion (a portion operable to positively lock with another component) operable to secure the connector pin 100 to the tubular connector sleeve 200. In the illustrated embodiments, the lock portion may be formed by a recess, e.g., a circumferential lock groove 122, formed in the outer surface 116 of the central portion 106. The lock groove 122 may engage a corresponding lock portion associated with the tubular connector sleeve 200 as further described below.

Figure 4:
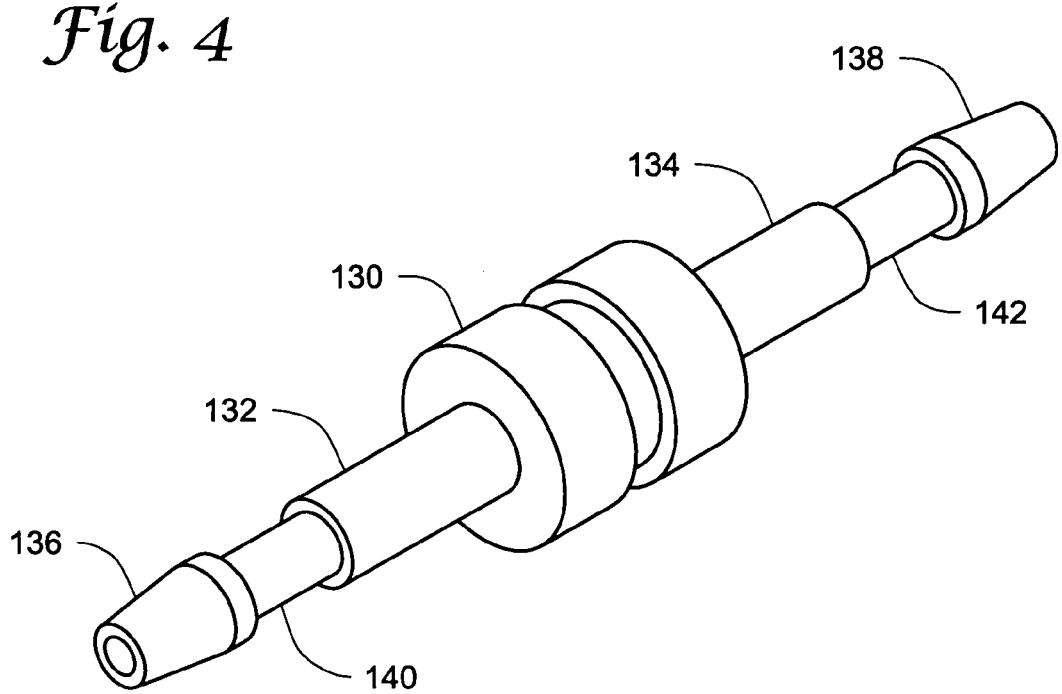
FIG. 4 is a perspective view of a connector pin in accordance with another embodiment of the present invention.

An alternative connector pin 130 illustrated in FIG. 4 (which is similar in many respects to the connector pin 100 described above) may include end portions 132 and 134 that have axial tapers 136 and 138, respectively. The axial tapers 136 and 138 may assist in insertion of the end portions 132 and 134 into receiving ends of the medical tubing. The end portions 132 and 134 may also include circumferentially depressed sections 140 and 142, respectively. The circumferentially depressed sections 140 and 142 may assist in securing the medical tubing to the end portions 132 and 134. That is, since medical tubing is typically made of a generally compliant material, the inner surface of the tubing (e.g., catheters 60 and 70 of FIG. 2) will generally comply with the surface of the end portions of the connector pin 130, including the depressed sections 140 and 142. Other connector pin embodiments may be similar to those described in U.S. Pat. No. 5,405,339 to Kohnen et al.

Figure 5:
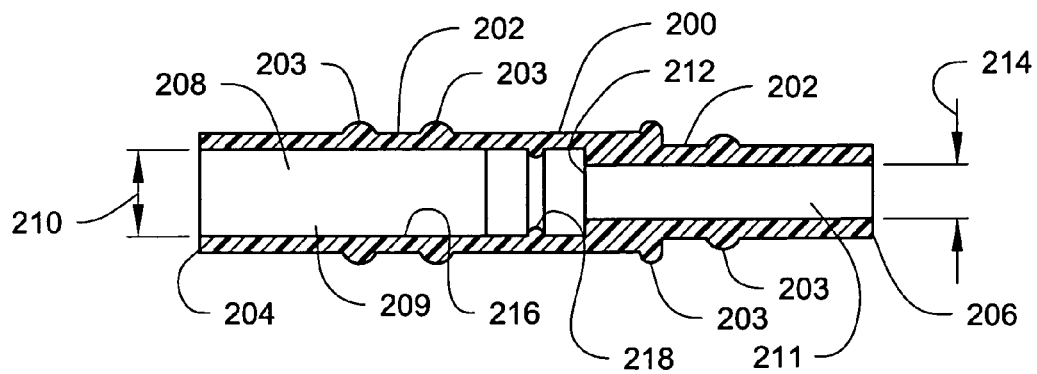
FIG. 5 is a cross-sectional view of a tubular connector sleeve in accordance with one embodiment of the invention.

FIG. 5 illustrates the exemplary tubular connector sleeve 200 of FIGS. 1 and 2. The connector sleeve 200 may be made of a flexible and resilient material operable to receive the catheters 60 and 70 and the connector pin 100 therein. Once assembled, the connector sleeve 200 may provide not only secure coupling of the mating components, but also strain relief to the catheter ends.

The connector sleeve 200 may include a passageway 208 extending from a first end 204 of the sleeve to a second end 206. In the illustrated embodiment, the passageway 208 is cylindrical and stepped. The step may be defined, for example, by providing a first section 209 of the passageway 208 extending from the first end 204 of the sleeve 200 to a stop surface 212 located within the passageway 208. The passageway 208 may, in the first section 209, have a first interfacing dimension, e.g., may be defined by a first diameter 210. The passageway 208 may also include a second section 211 that extends from the stop surface 212 to the second end 206 of the sleeve 200. The second section 211 may have a second interfacing dimension, e.g., may be defined by a second diameter 214. The first interfacing dimension of the passageway 208 may be greater than the second interfacing dimension, e.g., the first diameter 210 may be greater than the second diameter 214.

As used herein, the term "diameter" may refer to the length of the longest straight line segment passing through the center of a cross-section of a respective object, e.g., the passageway 208, and terminating at the object periphery, e.g., at the walls of the passageway. Thus, the term "diameter" may be used to describe an effective diameter of any component of the present invention (e.g., sleeve, sleeve passageway, connector pin, lumen, and tubing section) whether it has a circular or non-circular cross-sectional shape, e.g., oval.

While the shape of the passageway 208 is described and illustrated herein as including two generally uniform stepped bores, the actual shape of the passageway and, for that matter, the shape of the connector sleeve 200 itself, may be altered without departing from the scope of the invention.

The first section 209 of the sleeve 200 may be defined by an inner surface 216. The inner surface or wall 216 may include a lock portion, e.g., an inwardly extending protrusion 218. The protrusion 218 is preferably circumferential and operable to engage a mating lock portion, e.g., the lock groove 122 (see FIG. 3) of the connector pin 100, when the latter is correctly positioned within the connector sleeve (see FIG. 2).

The connector sleeve 200 may also include suture grooves 202. In the illustrated embodiment, the connector sleeve 202 may include two separate suture grooves 202 defined by outwardly extending circumferential protrusions 203.

The material used to make the connector sleeve 200 is preferably flexible and resilient. While various polymers are suitable, materials that achieve these objectives may include silicone and polyurethane. In other embodiments, the sleeve 200 could be made of a less compliant, e.g., relatively rigid, material.

Assembly of the connector assembly of FIGS. 1 and 2 will now be described with reference to FIGS. 6 and 7. These figures are cross-sectional views of the exemplary connector assembly 50 of FIGS. 1 and 2 in various stages of assembly. The connector assembly is described herein with respect to a drug or fluid medication delivery system using an implanted drug pump (not shown) operable to deliver drugs to a location within the brain. As stated above, however, this application is not limiting.

A catheterization procedure may begin with the placement of a distal catheter section (e.g., the catheter 70 of FIG. 2). This section of catheter may be inserted in a manner known to those skilled in the art. Before, during, or after proper placement of the distal section of the catheter 70 has been verified, a subcutaneous pump pocket may be prepared at the desired anatomical location within a patient's body. A proximal catheter section, e.g., catheter 60 of FIG. 2, may then be tunneled from the distal catheter section to the pump pocket. At this point in the procedure, the adjacent ends of the distal and proximal catheter sections, e.g., the coupling ends of catheters 60 and 70 that are shown in the Figures, may be connected using the connector assembly described herein.

Figure 6:
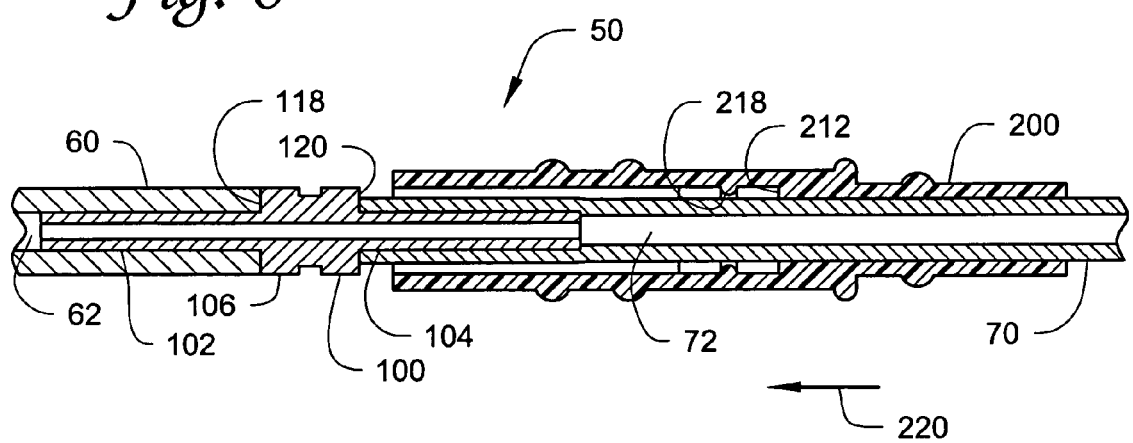

As represented in FIG. 6, the connector sleeve 200 may first be slid over the coupling end of the second catheter 70. The sleeve may be slid sufficiently onto the second catheter 70 to permit the physician unimpeded access to the coupling end of the second catheter. The second end portion 104 of the connector pin 100 (in some embodiments, the connector pin 100 may be symmetrical such that the first end portion 102 is identical to the second end portion) may be inserted into the lumen 72 of second catheter 70. The first end portion 102 may be similarly inserted into the lumen 62 of the first catheter 60.

The end portions 102 and 104 of the connector pin 100 are preferably inserted into their respective catheter sections 60 and 70 until they contact the respective tubing stop surfaces 118 and 120. In practice, the implanting physician may effect the catheter connections by grasping the enlarged central portion 106 of the connector pin 100.

The outer diameter of each end portion 102 and 104 may be slightly larger than the undeflected diameter of the lumens of the respective catheters 60 and 70. Alternatively, the outer diameters of the end portions 102 and 104 may be the same as, or slight less than, the diameters of the lumens of the respective catheters. The resulting fit between the components may result in not only secure connection of the catheters 60 and 70, but may also provide substantially leak-free flow of fluid between the catheters.

Figure 7:
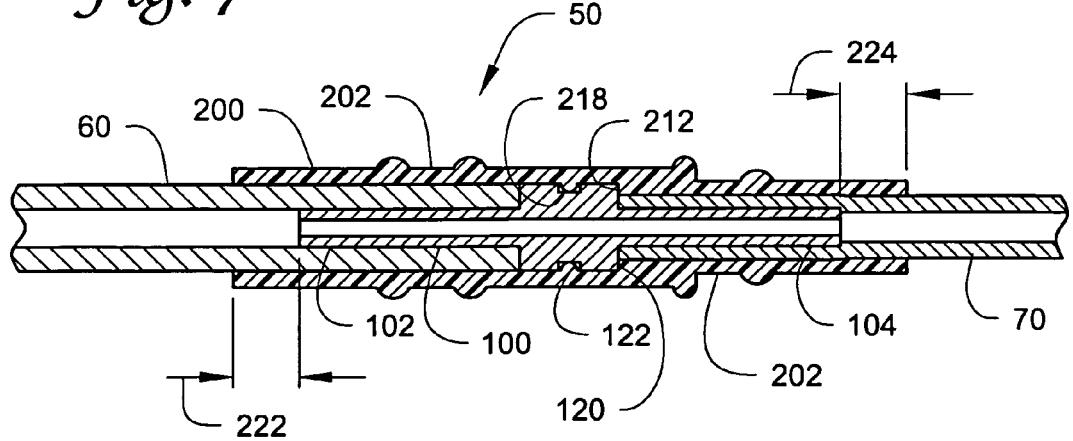

Once the catheters 60 and 70 are coupled to the connector pin 100 as generally illustrated in FIG. 6, the tubular connector sleeve 200 may be slid over the connector pin 100 in the direction 220 until the second stop surface 120 of the connector pin 100 contacts the stop surface 212 of the connector sleeve 200 as shown in FIG. 7. Prior to reaching the position illustrated in FIG. 7, the circumferential protrusion 218 of the sleeve 200 may traverse the central portion 106 of the connector pin 100 until the protrusion 218 reaches the lock groove 122, whereby the protrusion engages the lock groove as shown in FIG. 7.

The outer diameters of the catheters 60 and 70 may be slightly larger than the undeflected diameters 210 and 214 of the connector sleeve 200 (see FIG. 5). Similarly, the diameter 210 may be sized to receive the central portion 106 of the pin connector 100 therein as shown in the figures. In other embodiments, the diameters 210 and 214 may be the same as, or slightly larger than, the corresponding catheters 60 and 70 and the central portions 106. The resulting fit between the sleeve and the catheters 60 and 70 and pin connector 100 assists in securing the sleeve in place. Moreover, the abutting relationship of the stop surface 120 (of the connector pin 100) with the stop surface 212 (of the connector sleeve 200) provides means to ensure proper longitudinal positioning, e.g., self-location, of the sleeve relative to the pin. Still further, the engagement of the protrusion 218 of the sleeve 200 with the groove 122 of the connector pin 100 provides positive feedback to the physician during connection and further prevents longitudinal separation, e.g., pulling apart, of the catheters 60 and 70.

While the stop surface 212 is shown herein as being generally perpendicular to the axis of the sleeve 200, other embodiments may provide other surface configurations. For example, a tapered surface may be used to form the stop surface.

Once the connector assembly 50 has been assembled as shown in FIG. 7, it may be secured to surrounding tissue, e.g., sutured or ligated to scalp tissue, using the suture grooves 202. Preferably, a suture groove 202 is located over each side of the central portion 106, such that each catheter is effectively ligated by a suture.

The size of medical tubing connector assembly 50 may vary depending upon the size of the particular tubing to be connected. In one exemplary embodiment, the catheters 60 and 70 may have an undetected lumen diameter of about 0.02 to about 0.03 inches (in), e.g., about 0.024 in (0.61 millimeters (mm)). The connector pin 100 may have a length of about 0.5 in (13 mm), while the outer diameter of each end portion 102 and 104 may be about 0.024 in (0.61 mm). The outer diameter of the enlarged central portion 106 may be about 0.085 in (2.16 mm), while the outer diameter of the first catheter 60 and the second catheter 70 may be about 0.089 in (2.26 mm) and 0.041 in (1.04 mm), respectively. The sleeve 200 may have length of about 0.6 to about 1 in, e.g., about 0.8 in (20 mm), a first outer diameter (proximate the first end 204) of about 0.125 in (3.17 mm), a first inner diameter 210 of about 0.080 to about 0.10 in, e.g., about 0.094 in (2.4 mm), a second outer diameter (proximate the second end 206) of about 0.088 in (2.23 mm), and a second inner diameter 214 of about 0.035 to about 0.050 in, e.g., about 0.046 in (1.17 mm).

Connector assemblies in accordance with embodiments of the present invention may provide a secure method and apparatus for connecting separate sections of medical tubing by using a two-piece connector assembly (connector pin and connector sleeve). Moreover, connector sleeves in accordance with embodiments of the present invention provide not only secure coupling, but also strain relief to the catheter connection. For instance, when assembled, the sleeve 200 preferably extends a first distance 222 beyond the end of the first end portion 102 of the pin connector 100 (see FIG. 7) and a second distance 224 beyond the second end portion 104. That is, a longitudinal length of the connector sleeve 200 is preferably greater than a longitudinal length of the connector pin 100. This construction may reduce the chance of the pin connector 100 puncturing the catheters.

The complete disclosure of the patents, patent documents, and publications cited in the Background, the Detailed Description of Exemplary Embodiments, and elsewhere herein are incorporated by reference in their entirety as if each were individually incorporated.

Exemplary embodiments of the present invention are described above. Those skilled in the art will recognize that many embodiments are possible within the scope of the invention. Other variations, modifications, and combinations of the various components and methods described herein can certainly be made and still fall within the scope of the invention. Thus, the invention is limited only by the following claims and equivalents thereto.

What is claimed is:

1. A connector assembly for connecting sections of medical tubing, the assembly comprising:
   a connector pin comprising:
      a first end portion, a second end portion, and a lumen extending between the first end portion and the second end portion; and
      a central portion located between the first end portion and the second end portion, wherein the central portion has an outer diameter that is larger than an outer diameter of both the first and second end portions, and wherein the central portion is bounded by stop surfaces perpendicular to a longitudinal axis of the connector pin; and
   a tubular connector sleeve comprising a first end, a second end, and a passageway extending between the first end and the second end, the passageway comprising a stop surface that is perpendicular to an axis of the connector sleeve such that the passageway is defined by: a generally uniform bore having a first diameter extending between the first end of the sleeve and the stop surface of the passageway; and a generally uniform bore having a second diameter extending between the stop surface of the passageway and the second end of the sleeve, wherein the first diameter is greater than the second diameter.

2. The connector assembly of claim 1, wherein the sleeve comprises a polymer.

3. The connector assembly of claim 1, wherein the sleeve comprises one or more suture grooves on an exterior surface.

4. The connector assembly of claim 1, wherein each of the first end portion, the second end portion, and the central portion are substantially cylindrical in shape.

5. The connector assembly of claim 1, wherein a longitudinal length of the sleeve is greater than a longitudinal length of the connector pin.

6. A connector assembly for connecting sections of medical tubing, the assembly comprising:
   a connector pin comprising:
      a first end portion for insertion into a first section of medical tubing;
      a second end portion for insertion into a second section of medical tubing, wherein a lumen extending between the first end portion and the second end portion is operable to permit fluid communication between the first and second sections of medical tubing; and
      a central portion located between the first end portion and the second end portion, wherein the central portion has an outer diameter that is larger than an outer diameter of at least one of the first and second end portions, and wherein the central portion is bounded by stop surfaces generally perpendicular to a longitudinal axis of the connector pin; and
   a flexible connector sleeve operable to secure the first and second sections of medical tubing relative to the connector pin, the connector sleeve comprising a first end, a second end, and a stepped passageway extending between the first and second ends, the stepped passageway comprising:
   a first section comprising an inner surface defined by a bore of a first diameter, the bore of the first diameter extending both from an inwardly extending protrusion, formed along the inner surface of the first section of the stepped passageway, to the first end; and from the protrusion to a stop surface located within the stepped passageway; and
   a second section comprising an inner surface defined by a bore of a second diameter, the bore of the second diameter extending from the stop surface of the stepped passageway to the second end of the connector sleeve, wherein the first diameter is greater than the second diameter.

7. The connector assembly of claim 6, wherein the inwardly extending protrusion is operable to engage a groove formed on an outer surface of the central portion of the connector pin.

8. A catheter connector assembly comprising:
a connector pin having a lumen therein, the connector pin comprising:
 a first end portion for insertion into a first catheter;
 a second end portion for insertion into a second catheter; and
 a central portion located between the first end portion and the second end portion, wherein the central potion has an outer diameter that is larger than an outer diameter of one or both of the first and second end portions; and
a tubular strain relief sleeve operable to engage the first and second catheters and the connector pin, the sleeve comprising:
 a first end, a second end, and a passageway extending between the first end and the second end, the passageway comprising a stop surface located between the first end and the second end, wherein the passageway is further defined by a generally uniform bore of a first diameter extending from the stop surface of the passageway to the first end of the tubular strain relief sleeve, and a generally uniform bore of a second diameter extending from the stop surface of the passageway to the second end of the tubular strain relief sleeve, the first diameter being greater than the second diameter, and further wherein the stop surface is operable to abut the central portion of the connector pin when the connector assembly is assembled.

9. The connector assembly of claim 8, wherein the first diameter of the passageway is sized to receive the outer diameter of the central portion of the connector pin.

10. The connector assembly of claim 8, wherein the outer diameter of the central portion comprises a surface having a circumferential groove therein.

11. The connector assembly of claim 10, wherein the bore of the first diameter of the passageway is defined by a first inner surface, the first inner surface comprising an inwardly extending protrusion operable to engage the circumferential groove of the central portion.

12. The connector assembly of claim 8, wherein the sleeve comprises a polymer.

13. The connector assembly of claim 8, wherein the connector pin comprises a noble metal.

14. The connector assembly of claim 8, wherein a longitudinal length of the sleeve is greater than a longitudinal length of the connector pin.

15. A connector assembly for connecting sections of medical tubing, the assembly comprising:
a connector pin comprising:
 a first end portion, a second end portion, and a lumen extending between the first end portion and the second end portion; and
 a central portion located between the first end portion and the second end portion, wherein the central portion has an outer diameter that is larger than an outer diameter of both the first and second end portions, and wherein the central portion is bounded by stop surfaces generally perpendicular to a longitudinal axis of the connector pin; and
a tubular connector sleeve comprising a first end, a second end, and a passageway extending between the first end and the second end, the passageway defining a stop surface that is generally perpendicular to an axis of the connector sleeve such that the passageway is defined by: a generally uniform bore having a first diameter extending between the first end of the sleeve and the stop surface of the passageway; and a generally uniform bore having a second diameter extending between the stop surface of the passageway and the second end of the sleeve, wherein the first diameter is greater than the second diameter, and wherein the generally uniform bore of the first diameter comprises a first lock portion operable to engage a second lock portion formed on the central portion.

16. The connector assembly of claim 15, wherein the first lock portion comprises a protrusion extending inwardly from a wall of the passageway.

17. The connector assembly of claim 15, wherein the second lock portion is defined by a groove formed on the outer diameter of the central portion.

* * * * *

UNITED STATES PATENT AND TRADEMARK OFFICE
CERTIFICATE OF CORRECTION

PATENT NO.       : 7,331,613 B2                           Page 1 of 1
APPLICATION NO.  : 10/844962
DATED            : February 19, 2008
INVENTOR(S)      : Gregory T. Schulte It is certified that error appears in the above-identified patent and that said Letters Patent is hereby corrected as shown below:

Col. 9, Line 16, Claim 8: "potion" should be deleted - should read --portion--.

Signed and Sealed this

Eleventh Day of November, 2008

JON W. DUDAS
*Director of the United States Patent and Trademark Office*